United States Patent
Raupach

(10) Patent No.: US 10,424,090 B2
(45) Date of Patent: Sep. 24, 2019

(54) DETERMINING A SPATIAL DISTRIBUTION OF MATERIAL PROPERTY VALUES ON THE BASIS OF A SINGLE-ENERGY CT SCAN WITH THE AID OF AN ITERATIVE OPTIMIZATION METHOD

(71) Applicant: Siemens Healthcare GmbH, Erlangen (DE)

(72) Inventor: Rainer Raupach, Heroldsbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/609,052

(22) Filed: May 31, 2017

(65) Prior Publication Data
US 2017/0352166 A1    Dec. 7, 2017

(30) Foreign Application Priority Data
Jun. 2, 2016 (DE) .................. 10 2016 209 674

(51) Int. Cl.
G06K 9/00   (2006.01)
G06T 11/00  (2006.01)
(Continued)

(52) U.S. Cl.
CPC ............ G06T 11/005 (2013.01); A61B 6/032 (2013.01); G06T 7/0012 (2013.01); G06T 2211/424 (2013.01)

(58) Field of Classification Search
CPC ............ G06T 2211/424; G06T 7/0012; G06T 11/005; A61B 6/032
See application file for complete search history.

(56) References Cited

U.S. PATENT DOCUMENTS

| | | | |
|---|---|---|---|
| 2013/0108128 A1* | 5/2013 | Yu | G06T 11/006 382/131 |
| 2013/0329856 A1* | 12/2013 | Kuwahara | A61N 5/1039 378/62 |

(Continued)

FOREIGN PATENT DOCUMENTS

DE    102015225395 A1    6/2017

OTHER PUBLICATIONS

Wikipedia: Levenberg-Marquardt algorithm. Version vom 5.5. 2016.; 2016.

(Continued)

*Primary Examiner* — Amara Abdi
(74) *Attorney, Agent, or Firm* — Harness, Dickey & Pierce, P.L.C.

(57) ABSTRACT

A method for determining a spatial distribution of a material property value in an examination region of an examination object is described. With an embodiment of the method, projection scan data is acquired which has been produced with the aid of a single-energy CT scan with a defined X-ray energy spectrum from the examination region of the examination object using a defined scan projection geometry. Furthermore, a target function is established which includes a spectral forward projection of the sought spatial distribution and the acquired projection data. Finally, a spatial distribution of a material property value is determined for which the target function assumes an extremal value. A material property distribution-determining device is also described. A computer tomography system is described, moreover.

26 Claims, 5 Drawing Sheets

(51) Int. Cl.
*A61B 6/03* (2006.01)
*G06T 7/00* (2017.01)

(56) References Cited

U.S. PATENT DOCUMENTS

| | | | | |
|---|---|---|---|---|
| 2014/0328448 | A1* | 11/2014 | Wu | G06T 7/0012 |
| | | | | 378/4 |
| 2015/0117595 | A1* | 4/2015 | Flohr | A61B 6/482 |
| | | | | 378/5 |
| 2016/0134852 | A1* | 5/2016 | Gao | G06T 5/001 |
| | | | | 348/745 |
| 2017/0172533 | A1 | 6/2017 | Raupach | |

OTHER PUBLICATIONS

Williamson, Jeffrey F. et al.: "On two-parameter models of photon cross sections; Application to dual-energy CT imaging", In: Med. Phys., vol. 33, No. 11, Nov. 2006, pp. 4115-4129, DOI:10.1118/1.2349688.

Long Y. et al.: "Two-Material Decomposition From a Single CT Scan Using Statistical Image Reconstruction"; Verfügbar online unter http://web:eecs.umich.edu/-fessler/papers/files/talk/11/aapm-long.pdf (abgerufen am Feb. 17, 2017); 2011.

German Office Action dated Feb. 17, 2017.

* cited by examiner

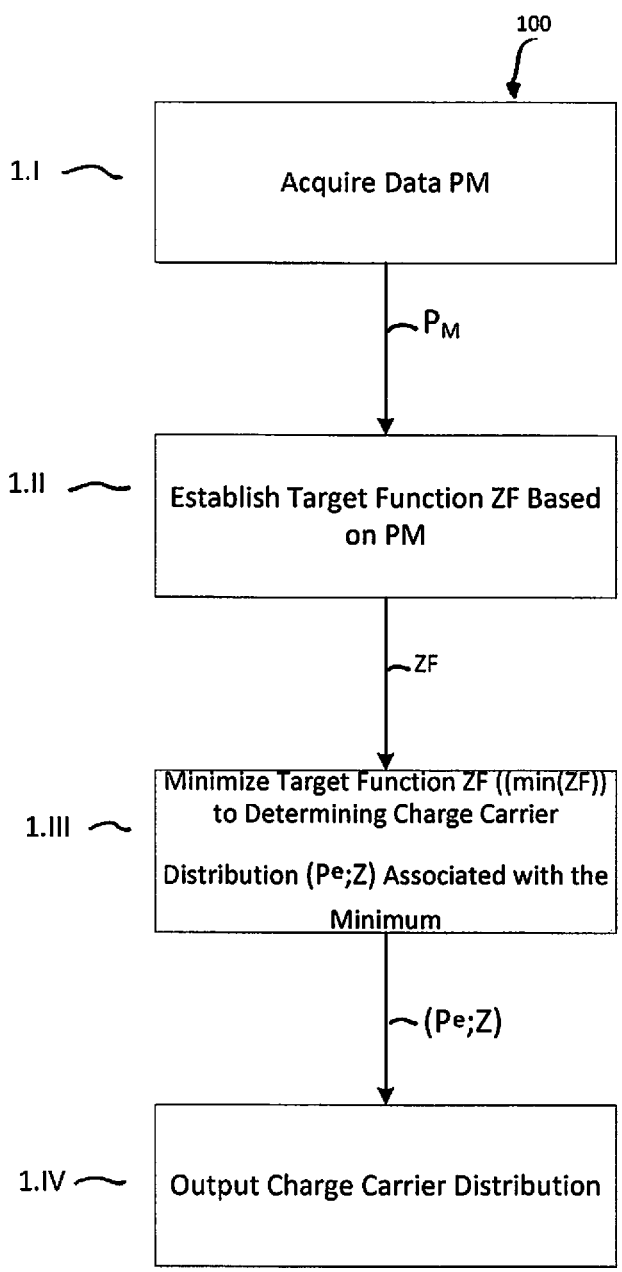

FIG 2

```
1.IIIa ── [ I_M = Q P_M ]
              │
         (ρ_e; Z)_0 ── ρ_e, M1
                    ── ρ_e, M2
         k = 0      ── Z_M1
1.IIIb             ── Z_M2
              │
              ▼
1.IIIba ── [ Determine Estimated Values of
             Electron and Nuclear
             Charge Carrier Density Distributions ]   ◄── (ρ_e; Z)_k
              │
         h_z(I_k) ── h_ρ(I_k)
         (ρ_e; Z)_k ── h_ρ(I_M)                [ k = k+1 ]
                   ── h_z(I_M)
              │                                   1.IIIbe
              ▼
1.IIIbb ── [ Determine Correction Term ]
              │
         (ρ_e; Z)_k ── (Δρ_e; ΔZ)_k
              │
              ▼
1.IIIbc ── [ Determine First Approximated
             Charge Carrier Distribution ]       ── (ρ_e; Z)_k+1
              │
         (ρ_e; Z)_k+1
              │
              ▼
1.IIIbd ── < P_M − P_S{(ρ_e; Z)_k+1} <= SW? > ── n
              │ j
              ▼
         (ρ_e; Z)_k+1
              │
              ▼
1.IIIc ── [ (ρ_e; Z) = (ρ_e; Z)_k+1 ]
```

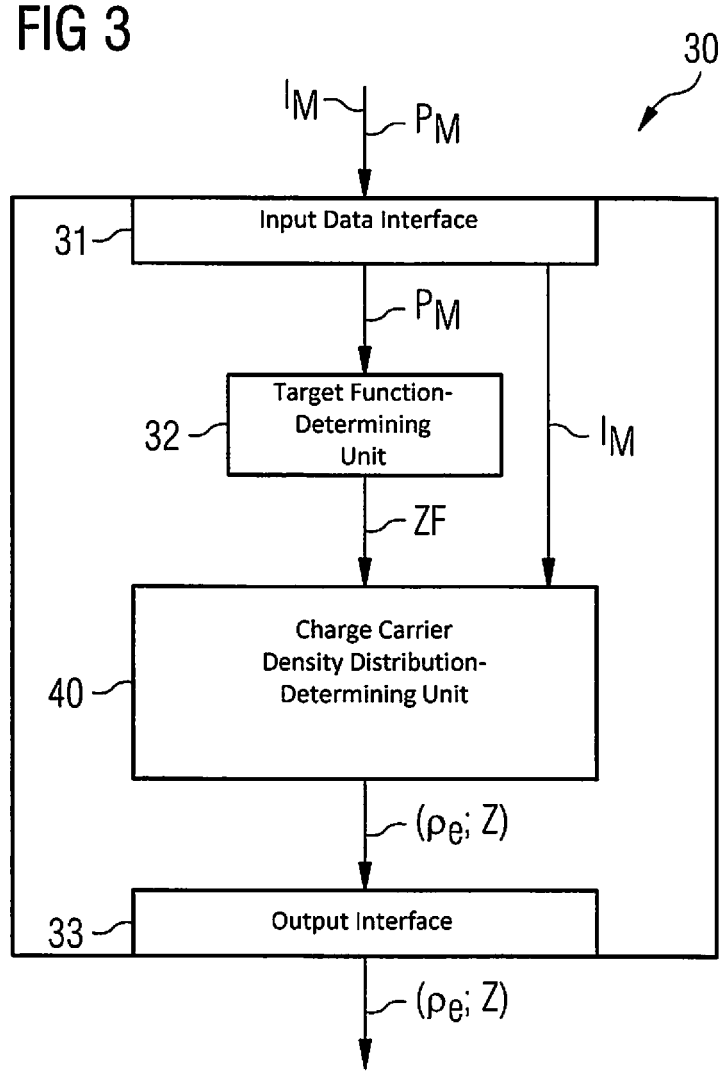

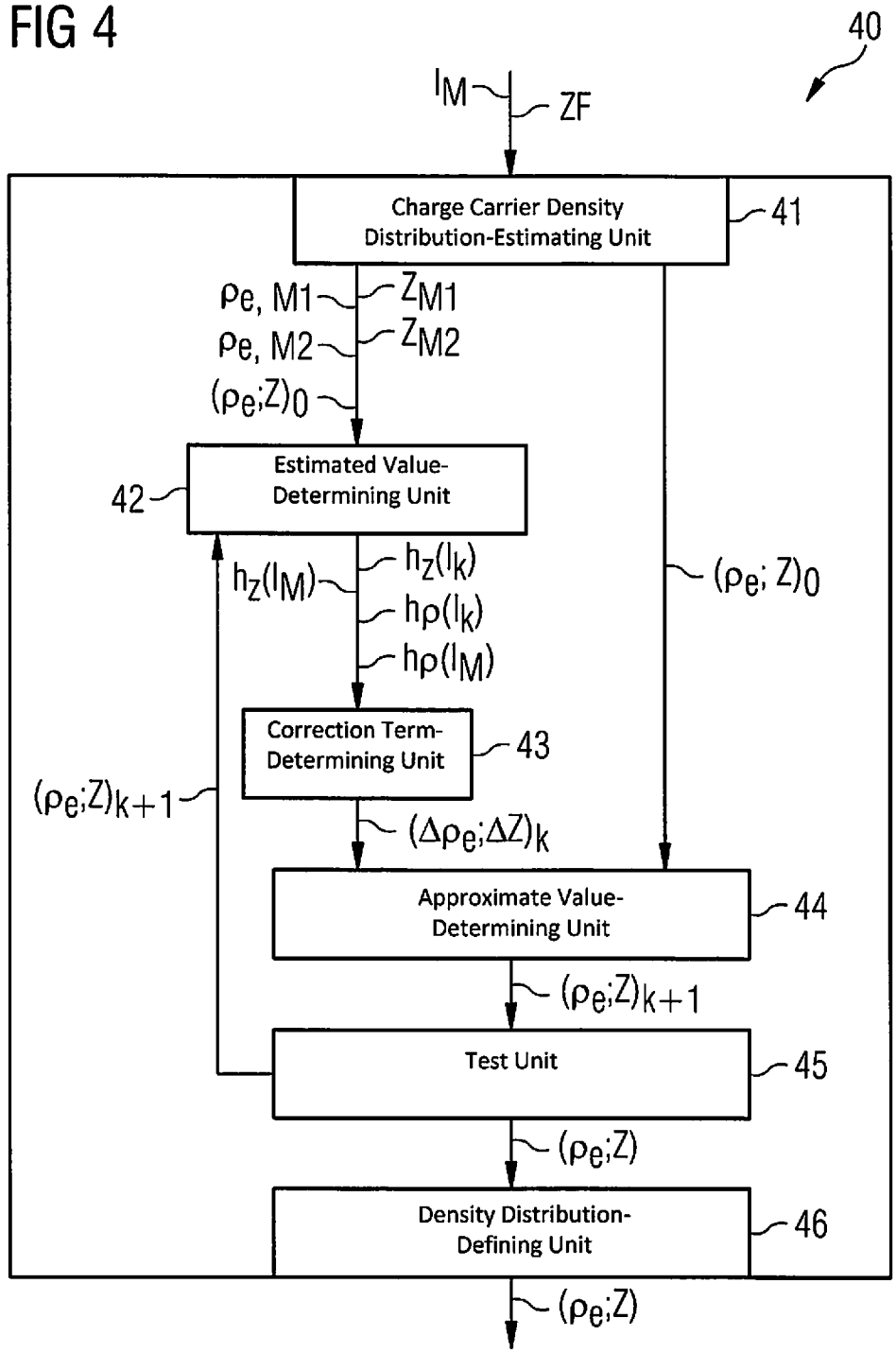

DETERMINING A SPATIAL DISTRIBUTION OF MATERIAL PROPERTY VALUES ON THE BASIS OF A SINGLE-ENERGY CT SCAN WITH THE AID OF AN ITERATIVE OPTIMIZATION METHOD

PRIORITY STATEMENT

The present application hereby claims priority under 35 U.S.C. § 119 to German patent application number DE 102016209674.5 filed Jun. 2, 2016, the entire contents of which are hereby incorporated herein by reference.

FIELD

At least one embodiment of the invention generally relates to a method for determining a spatial distribution of a material property value in an examination region of an examination object. Furthermore, at least one embodiment of the invention generally relates to a material property distribution-determining device. At least one embodiment of the invention generally relates, moreover, to a computer tomography system.

BACKGROUND

With radiation therapy, radiological data is acquired, for example with the aid of CT scans, for planning the irradiation of a patient in order to be able to define the radiation dose for the planned irradiation. In particular, it is important to define radiation doses in a spatially resolved manner in order to destroy only malignant tissue in the region to be irradiated and to spare neighboring, potentially very sensitive regions in the body of the patient.

The interactions between radiation and tissue that occur during irradiation of the patient can be divided into primary and secondary effects. The primary effects are the direct interaction of the radiation with the tissue. In the case of irradiation with photons, the interaction primarily occurs with electrons. If tissue with heavy particles is irradiated, then the interaction primarily occurs with the atomic nuclei. In addition, in the case of the described primary processes, so much energy is transferred to the electrons during the interaction that they are released from the molecule and have enough energy themselves to cause further ionization processes as a secondary effect. Different effects occur when electromagnetic radiation interacts with electrons. In the case of absorption of radiation in soft tissue, which is primarily composed of water, the Compton effect dominates; in the case of absorption in solid body substance, such as, for example, bone substance, the photo effect dominates.

To be able to determine the radiation dose in advance, the charge carrier density distribution, i.e. in particular the electron density distribution, or the nuclear charge carrier density distribution of the materials present in the region to be examined must be known.

A conventional method for determining electron densities using CT image data sets consists in mapping attenuation values of the CT image data, hereinafter also called CT values for short, on electron densities with the aid of a simple table. However, this method does not achieve a very high level of accuracy because in the case of the polychromatic X-ray radiation used in CT scans, CT values of the same material in the image are dependent on the size of the object to be examined in which they are scanned, and are also dependent on the position in the cross-section of the object. This is due to the fact that, owing to the increased radiation hardness, a near-surface volume element is exposed to a softer radiation during imaging than a centrally located volume element. With the same density and material, a higher CT value (stronger attenuation) is therefore associated with the near-surface volume element than with the centrally located volume element. Owing to the different CT values, a higher electron density is therefore associated with the near-surface volume element than the centrally located volume element. The accuracy of this method is therefore also limited if a calibration has previously been carried out with the aid of a test body (what is known as a phantom) in a very accurate and reproducible manner.

Another way of determining charge carrier densities is based on the CT scan with the aid of two spectra, also called dual-energy CT, wherein the recorded scan data is depicted in a base material breakdown. The scan data divided according to individual materials can then be mapped again on charge carrier densities. As already mentioned, the absorption properties of the biologically relevant materials are essentially based on just two different effects, the photo effect and the Compton effect, so a breakdown of the scan data according to two base materials, for example water or soft tissue and calcium, is sufficient. In this way, the effect of the patient's size and the position of a volume element in the body of the patient is reduced for these materials.

However, not every CT device has the option of a dual-energy scan, so this method is only available to a limited extent.

SUMMARY

The inventor recognizes that there is a problem of developing a more precise method for determining a material property distribution, in particular a charge carrier density distribution, in a region to be examined of an examination object, which also works with the application of a single-energy CT system for the pre-scan. In this context, a single-energy CT system should be taken to mean a CT system with which a scan can be carried out with X-ray radiation with just a single defined X-ray energy spectrum.

At least one embodiment is directed to a method for determining a material property distribution in an examination region of an examination object; at least one embodiment is directed to a material property distribution-determining device; and at least one embodiment is directed to a computer tomography system.

In at least one embodiment of the inventive method, for determining a spatial distribution of a material property value in an examination region of an examination object, projection scan data is acquired which has been produced with the aid of a single-energy CT scan with a defined X-ray energy spectrum from the examination region of the examination object using a defined scan projection geometry. The defined X-ray energy spectrum can be determined with the aid of a calibration scan with an X-ray energy spectrum that is to be used later using a phantom. It can also be calculated on the basis of the known technical data of the CT system used.

In at least one embodiment, the inventive material property distribution-determining device has a projection scan data acquisition unit for acquiring projection scan data which has been produced with the aid of a single-energy CT scan with a defined X-ray energy spectrum from the examination region of the examination object using a defined scan projection geometry. Part of at least one embodiment of the inventive material property distribution-determining device is a target function determining unit, moreover, for establishing a target function, which comprises a forward projection of a sought spatial distribution of a material property value and the acquired projection scan data. At least one embodiment of the inventive material property distribution-determining device comprises, moreover, a material property distribution-determining unit for determining a spatial distribution of a material property by optimizing the target function in such a way that the target function assumes an extremal value, preferably a minimum value.

At least one embodiment of the inventive computer tomography system has a scanning unit for scanning an examination region of an object to be examined, a controller for controlling the scanning unit and at least one embodiment of an inventive material property distribution-determining device. In this case, the projection scan data recorded by the computer tomography system and reconstructed image data from an examination region of an examination object is processed directly by the controller to the extent that a material property distribution is determined therefrom. Since the material property distribution-determining device is integrated directly in the computer tomography system, no additional devices are required to determine a material property distribution.

An implementation largely in terms of software has the advantage that even previously used controllers of computer tomography systems or even other computer systems used for analysis and evaluation can be easily upgraded by way of a software update in order to work inventively. In this respect at least one embodiment is also directed to a corresponding computer program product having a computer program which can be loaded directly into a storage device of at least one embodiment of an inventive computer tomography system or another arithmetic unit, having program segments to carry out all steps of at least one embodiment of the inventive method when the computer program is run in the computer tomography system or another arithmetic unit used for evaluation of the projection scan data and image data produced by the computer tomography system.

In addition to the computer program, a computer program product of this kind can optionally comprise additional components, such as, e.g. documentation and/or additional components also hardware components, such as, e.g. hardware keys (dongles, etc.), for use of the software.

A computer-readable medium, for example, a memory stick, a hard disk or another transportable or permanently installed data carrier, on which the program segments of the computer program that can be read and executed by an arithmetic unit are stored, can be used for transport to the storage device of the computer tomography system or the arithmetic unit and/or for storing on the computer tomography system or the arithmetic unit. For this purpose the arithmetic unit can have, e.g., one or more collaborating microprocessor(s) or the like.

BRIEF DESCRIPTION OF THE DRAWINGS

The invention will be described in more detail once again below with reference to the accompanying figures and referring to example embodiments. In the figures:

FIG. 1 shows a flow diagram which illustrates a method for determining a charge carrier distribution according to an example embodiment of the invention, FIG. 2 shows a flow diagram with which an optimization step of the method illustrated in FIG. 1 is shown in detail, FIG. 3 shows a block diagram which illustrates a charge carrier density distribution-determining device according to an example embodiment of the invention, FIG. 4 shows a block diagram which illustrates a charge carrier density distribution-determining unit according to an example embodiment of the invention.

DETAILED DESCRIPTION OF THE EXAMPLE EMBODIMENTS

Figure 5:
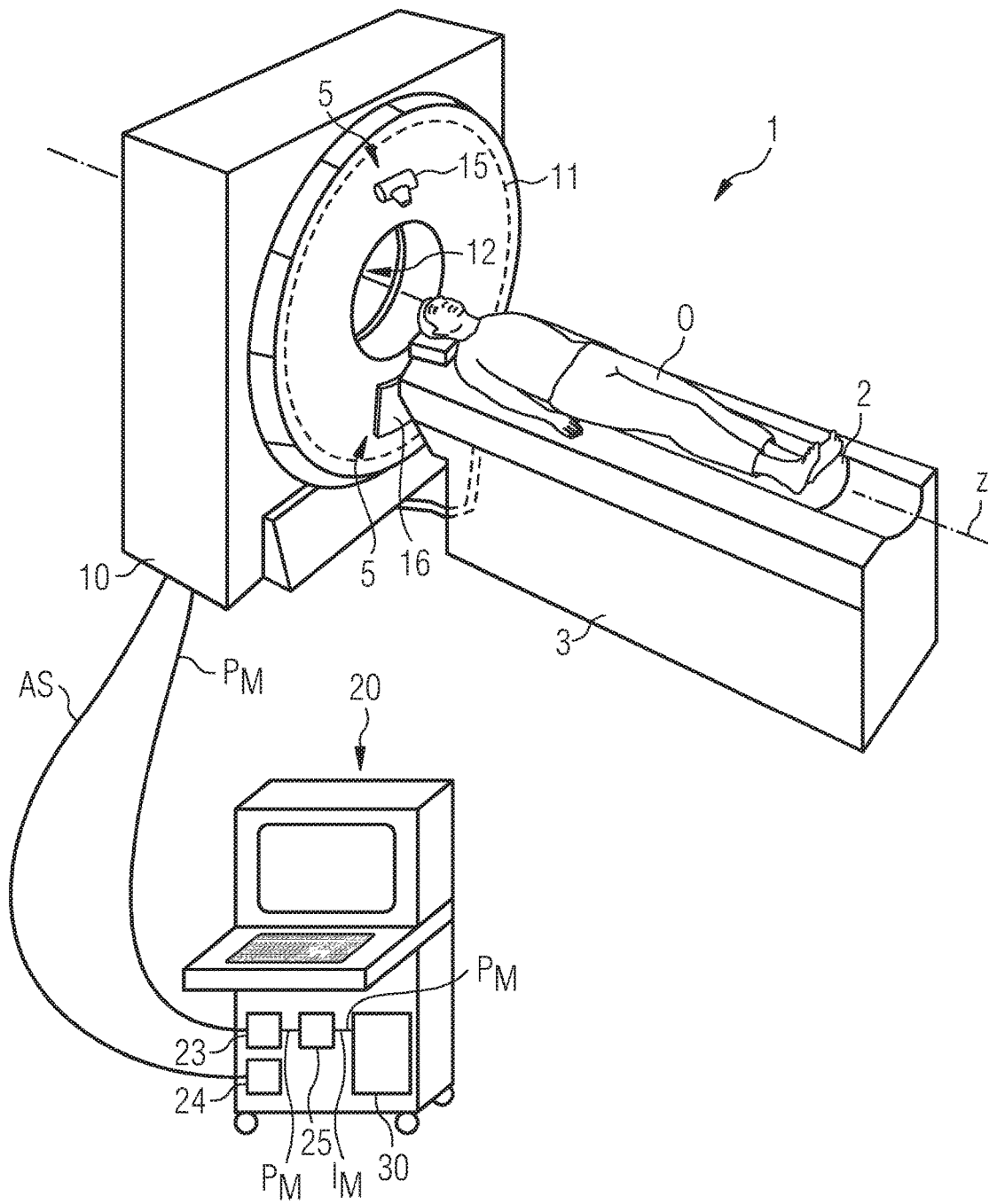
FIG. 5 shows a computer tomography system having a charge carrier density distribution-determining device according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment of the inventive method, for determining a spatial distribution of a material property value in an examination region of an examination object, projection scan data is acquired which has been produced with the aid of a single-energy CT scan with a defined X-ray energy spectrum from the examination region of the examination object using a defined scan projection geometry. The defined X-ray energy spectrum can be determined with the aid of a calibration scan with an X-ray energy spectrum that is to be used later using a phantom. It can also be calculated on the basis of the known technical data of the CT system used.

A defined scan projection geometry should be taken to mean that the parameters of the CT scan arrangement influencing projection scan data are known. By way of example, the arrangement of the examination object in the scan space, the spacings between the examination region, the X-ray source and the detector, the form of the X-ray beam of the X-ray source and the X-ray energy spectrum already mentioned should be known.

Projection scan data should, as usual, be taken to mean absorption data which has been recorded from the examination region of the examination object from different recording angles. A projection scan data space is associated with this projection scan data. If an image is to be produced from the projection scan data, then the projection scan data has to be transformed into the image data space. This can occur, for example, by way of a filtered back projection of the projection scan data.

Within the scope of at least one embodiment of the inventive method, a target function is also established which comprises a spectral forward projection of the sought spatial distribution with the aid of a spectral forward projector and the acquired projection data. In this context, spectral forward projection should be taken to mean a projection of the image data space into the projection scan data space which takes into account the spectral distribution of the X-ray radiation when determining projection data. Determination of the spectral forward projector also includes, for example, the form of the X-ray energy spectrum and possible form filters which can increase the hardness of the X-ray radiation. In addition, further effects, such as, for example, scatter radiation effects, which affect the spectrum of the X-ray radiation absorbed in the examination region, can also be taken into account when determining the spectral forward projector. The spectral forward projector can be determined using a phantom, for example, with the aid of a calibration scan with an X-ray energy spectrum that is to be used later. Alternatively the spectral forward projector can also be determined by a numeric simulation by taking into account the defined X-ray spectrum.

With the aid of the spectral forward projection, line integrals are calculated from a material property distribution, for example an electron density and/or an atomic charge distribution, for the X-ray spectrum used by taking into account the physical absorption processes, for example the photo effect and the Compton effect, which integrals represent the absorption of the X-ray radiation along the projection line or wayline of the respective line integral.

A base material breakdown forms a basis for calculation of the line integrals or of the spectral forward projector, wherein the base materials are chosen according to specific absorption mechanisms. For example, a first base material can have an absorption mechanism which is based on the Compton effect and a second base material can have an absorption mechanism which is based on the photo effect. The absorption of the X-ray radiation along the projection lines can be calculated on the basis of the initially still unknown distribution, and the absorption mechanisms allocated to the base materials. The distribution of the base materials corresponds precisely to the sought material property distribution or correlates therewith.

A kind of comparative value between the spectral forward projection and the projection scan data acquired with the aid of a single-energy CT scan is calculated with the target function.

Finally, a spatial distribution of a material property value is determined by optimizing the target function. An extremal value of the target function is determined. The extremal value is preferably a minimum value. Alternatively, the extremal value can also be a maximum value. The determined spatial distribution of a material property value is finally regarded as the sought spatial distribution of the material property value. In this context, a material property should be taken to mean a property of one or more material (s) which are correlated with the absorption of the X-ray radiation used for recording the CT projection scan data.

With at least one embodiment of the inventive method, the accuracy of determining material property distributions is significantly improved compared to conventional methods for determining distributions of material property values on the basis of single-energy CT data. This is achieved because the dependency of the determined material property distributions, e.g. the electron density distribution of a material, on the position in the cross-section of the total object is reduced. A more stable determination of material property distributions is possible thereby with, in general, variable position of the same materials in the field of view of the CT arrangement.

Furthermore, at least one embodiment of the inventive method has the advantage that a variable radiation quality can be better taken into account as a function of the position in the field of view, as is caused, for example, by a form filter, since the variability is also included when determining the spectral forward projector. In addition to the different radiation hardening owing to a variable radiographic length of the cross-section of the examination object itself, this is a further factor which can affect the dependency of the determined CT values, i.e. the image data, on the position in the cross-section or in the field of view.

In at least one embodiment, the inventive material property distribution-determining device has a projection scan data acquisition unit for acquiring projection scan data which has been produced with the aid of a single-energy CT scan with a defined X-ray energy spectrum from the examination region of the examination object using a defined scan projection geometry. Part of at least one embodiment of the inventive material property distribution-determining device is a target function determining unit, moreover, for establishing a target function, which comprises a forward projection of a sought spatial distribution of a material property value and the acquired projection scan data. At least one embodiment of the inventive material property distribution-determining device comprises, moreover, a material property distribution-determining unit for determining a spatial distribution of a material property by optimizing the target function in such a way that the target function assumes an extremal value, preferably a minimum value.

At least one embodiment of the inventive computer tomography system has a scanning unit for scanning an examination region of an object to be examined, a controller for controlling the scanning unit and at least one embodiment of an inventive material property distribution-determining device. In this case, the projection scan data recorded by the computer tomography system and reconstructed image data from an examination region of an examination object is processed directly by the controller to the extent that a material property distribution is determined therefrom. Since the material property distribution-determining device is integrated directly in the computer tomography system, no additional devices are required to determine a material property distribution.

The fundamental components of at least one embodiment of the inventive material property-determining device can be configured for the most part in the form of software components. This relates, in particular, to parts of the projection scan data acquisition unit, the target function determining unit and the material property distribution-determining unit. Basically, these components can, however, in part, also be implemented in the form of software-assisted hardware, for example FPGAs or the like, in particular when particularly fast calculations are involved. The necessary interfaces, for example when only an acquisition of data from other software components is involved, can likewise be designed as software interfaces. They can, however, also be designed as interfaces constructed in terms of hardware which are controlled by appropriate software.

An implementation largely in terms of software has the advantage that even previously used controllers of computer tomography systems or even other computer systems used for analysis and evaluation can be easily upgraded by way of a software update in order to work inventively. In this respect at least one embodiment is also directed to a corresponding computer program product having a computer program which can be loaded directly into a storage device of at least one embodiment of an inventive computer tomography system or another arithmetic unit, having program segments to carry out all steps of at least one embodiment of the inventive method when the computer program is run in the computer tomography system or another arithmetic unit used for evaluation of the projection scan data and image data produced by the computer tomography system.

In addition to the computer program, a computer program product of this kind can optionally comprise additional components, such as, e.g. documentation and/or additional components also hardware components, such as, e.g. hardware keys (dongles, etc.), for use of the software.

A computer-readable medium, for example, a memory stick, a hard disk or another transportable or permanently installed data carrier, on which the program segments of the computer program that can be read and executed by an arithmetic unit are stored, can be used for transport to the storage device of the computer tomography system or the arithmetic unit and/or for storing on the computer tomography system or the arithmetic unit. For this purpose the arithmetic unit can have, e.g., one or more collaborating microprocessor(s) or the like.

The claims and the following description each contain particularly advantageous embodiments and developments of the invention. In particular, the claims of one category can also be developed analogously to the dependent claims of a different category. Furthermore, within the scope of the invention the various features of different example embodiments and claims can also be combined to form new example embodiments.

In one embodiment of the inventive method, the spatial distribution of a material property value can be presented as a distribution based on the distribution of at least two different base materials. This is given, for example, when determining charge carrier distributions in the human tissue. The base materials are advantageously chosen such that they are associated with mutually independent mechanisms which each contribute to the material property value or its distribution.

The spatial distribution of a material property value preferably has a charge carrier density distribution, preferably a density distribution of electrons and/or nuclear charges, preferably of at least two different materials. Knowledge of the electron density distribution in an examination region of an examination object can be used, for example, when calculating the dose in radiotherapy.

If there is a plurality of different materials having different absorption behaviors in an examination region, then the distribution of the different materials can be determined only inaccurately using conventional methods in the case of a single-energy CT scan. This, in turn, conventionally also leads to inaccurate determination of the material property distributions.

According to at least one embodiment of the invention, the distribution of the material properties is used as a direct basis, wherein the distribution of the materials which is initially known only inaccurately on the basis of the image data is itself only used for determining starting values and estimated values, as will be described in more detail hereinafter. The effect of an inaccurately known distribution of different materials on the end result is therefore advantageously reduced or cancelled. At least one embodiment of the inventive method is particularly effective in the presence of two different materials, for example soft tissue and bone material, which are associated with different absorption mechanisms, in this case the Compton effect and the photo effect, which occur in the case of the single-energy CT scan. When determining the spectral forward projector, a division into two base materials having different absorption mechanisms is assumed, wherein this distribution is initially known only accurately. The different absorption mechanisms associated with the two base materials are taken into account for calculation of the absorption in the direction of the projection lines of the spectral forward projector. Finally, the initially only estimated distribution of the base materials is approximated to the actual distribution by comparison of the projection data determined with the aid of the forward projector with the projection scan data.

In principle, more than two different absorption mechanisms can also be taken into account in at least one embodiment of the inventive method, wherein the number of base materials increases in this case. For example, a K-edge absorption can also be taken into account in addition to the Compton effect and the photo effect.

In a preferred embodiment of the inventive method, a projection geometry corresponding to the scan projection geometry of the acquired projection scan data is assumed for the spectral forward projection. By way of the spectral forward projection, line integrals, whose values correspond to an absorption of the X-ray radiation in the respective projection direction, can be calculated from a spatial distribution of a material property value for a predetermined X-ray spectrum by taking into account the physical absorption processes in the absorption of the X-ray radiation.

According to at least one embodiment of the invention, the fact that the values of these line integrals have to correspond exactly to the attenuation values of the projection scan data in the case of a correctly determined material property distribution, or have to approximate these in the case of an approximately determined distribution, is then used. This fact is incorporated in the target function, which comprises precisely this described spectral forward projection of the sought spatial distribution and the acquired projection scan data.

In at least one embodiment of the inventive method, the step of determining the sought spatial distribution of a material property value, for which the target function assumes an extremal value, preferably comprises the application of an iterative approximation method, preferably a gradient descent method. A minimum of a convex function with a set of definitions, which is a subset of an n-dimensional vector space, can be determined particularly quickly with the aid of a gradient descent method.

With at least one embodiment of the inventive application, the sought material property distribution is accordingly precisely the point in the n-dimensional vector space at which the sought extremal value, preferably the sought minimum, of the target function being considered is located. Alternatively, other known non-linear optimization methods can also be applied.

In at least one embodiment of the inventive method, the target function particularly preferably comprises a standard of a difference of a spectral forward projection of a spatial distribution of a material property value and the acquired projection scan data. Since the set of projection scan data and the data set obtained with the aid of the spectral forward projection are each vectorial quantities, forming a standard across the two quantities allows a scalar comparative quantity to be formed whose extremal value, preferably a minimum, is associated with the sought material property distribution.

In a variant of at least one embodiment of the inventive method that can be applied particularly advantageously, a start distribution of a material property value is used in the course of the approximation method as an approximated spatial distribution of a material property value in a first iteration step and a correction term is determined for further iterative approximation to the sought spatial distribution of a material property value. The still very roughly estimated start distribution is gradually corrected with the aid of the correction term, so in the course of the iterative process there is a gradual approximation to the sought material property distribution.

In a particularly advantageous embodiment of the inventive method, the correction term has a transposed spectral forward projection of a difference of the acquired projection scan data and a spectral forward projection of the approximated spatial distribution of a material property value. In the course of a gradient descent method the correction term comprises precisely the gradient of the target function multiplied by an increment a.

Within the scope of a preferred variant of at least one embodiment of the inventive method, the correction term is approximately determined on the basis of estimated values of the spatial distribution of a material property value. The estimated values of the spatial distribution of a material property value can be determined on the basis of image data, which was reconstructed on the basis of the acquired projection scan data, and on the basis of comparative values, which were obtained by a spectral forward projection and a subsequent filtered back projection of the spatial distribution of a material property value currently approximated in the respective iteration step. While the reconstructed image data is defined by the acquired projection scan data and is therefore unchangeable, the comparative values, which were obtained by a spectral forward projection and a subsequent filtered back projection of the spatial distribution of a material property value currently approximated in the respective iteration step, are dependent on the currently discovered approximated distribution. If the iterative process converges towards the sought extremal value, preferably a minimum, then the values of the reconstructed image data and comparative data approximate each other until the correction term tends towards the value zero or falls below a predetermined threshold value, i.e. a further iteration does not bring any further improvement in the accuracy of the determined material property distribution.

In one embodiment of the inventive method, the iteration is terminated and the last-determined approximated spatial distribution of a material property value is defined as the sought spatial distribution of a material property value if a standard of the difference of a spectral forward projection of the approximated spatial distribution of a material property value and the acquired projection scan data falls below a predetermined threshold value. This is the case if the value of the correction term falls below a threshold value, so a continued iteration does not bring any further notable change in the approximately determined spatial distribution of a material property value.

FIG. 1 shows a flow diagram 100 which illustrates a method for determining a spatial distribution of a material property value, in this specific example a charge carrier density distribution, according to an example embodiment of the invention. In step 1.I single-energy CT projection scan data PM of an examination region of an examination object, for example of a patient, is firstly acquired. This can be acquired from the examination object, for example directly by a CT scan, or also emanate from a database in which CT image data from the relevant examination region of the examination object is stored. In step 1.II a target function ZF is then established on the basis of the acquired projection scan data PM, which function is as follows:

$$ZF = \|P_S\{\rho_e(x,y,z); Z(x,y,z)\} - P_M\|^2. \quad (1)$$

Here $\rho_e(x, y, z)$ is the sought electron density distribution, $Z(x, y, z)$ the sought distribution of the nuclear charges and $P_S$ corresponds to a spectral forward projector in the same geometry as the projection of the acquired projection scan data $P_M$ which calculates line integrals from an electron density and an atomic charge distribution for the X-ray spectrum used by taking into account the physical absorption processes.

Assuming a physically ideal absorption due solely to Compton and photo effects, the result of the forward projection $P_S$ for the $k^{th}$ scan value with ray $s_k$ can be presented as $$P_S\{\rho_e(x, y, z); Z(x, y, z)\}(k) = \int_0^\infty \left[ \int_{s_k} (\mu_{Compton}(\rho_e(x, y, z); E) + \mu_{Photo}(\rho_e(x, y, z); Z(x, y, z); E)) d\vec{s} \right] S_k(E) dE$$

Here:

$\mu_{Compton}$ ($\rho_e$ (x,y,z); E): is absorption due to the Compton effect at location (x, y, z) with energy E. The function $\mu_{Compton}$ ($\rho_e$(x,y,z);E) is known to a person skilled in the art and can either be analytically modeled or numerically tabulated.

$\mu_{Photo}(\rho_e$(x,y,z),Z(x,y,z);E): is absorption due to the photo effect at location (x, y, z) with energy E. The function $\mu_{Photo}$ ($\rho_e(x,y,z), Z(x,y,z); E$) is known to a person skilled in the art and can either be analytically modeled or numerically tabulated.

$S_k$ (E): is a standardized effective X-ray spectrum free air for the ray k, i.e.

$$\int_0^\infty S_k(E)dE = 1.$$

In reality, optionally additional effects such as scatter radiation, non-linear response of detectors, etc. should be considered.

The association between the distribution of the base materials as "material having characteristic absorption properties" and the charge carrier densities is therefore clear. Use of the charge carrier densities ($\rho$; Z) and the division into base materials, wherein a first base material represents a notional pure Compton material and a second base material represents a notional pure photo effect material, is therefore completely equivalent. The two representations can each be transformed into each other by a linear transformation. The person skilled in the art therefore knows how the spectral forward projector has to be constructed depending on the basis.

In step 1.III the target function ZF is finally minimized, with the argument ($\rho_e$; Z) associated with the minimum of the target function ZF corresponding to the sought charge carrier density distribution:

$$(\rho_e(x, y, z); Z(x, y, z)) = \underset{(\rho_e', Z')}{\mathrm{argmin}}(ZF(\rho_e'(x, y, z); Z'(x, y, z))). \quad (2)$$

Here, in the search for the minimum of the target function ZF, the argument thereof, the charge carrier function ($\rho_e''$; Z''), is varied until the minimum and the charge carrier distribution ($\rho_e$; Z) associated with this minimum is found.

In a step 1.IV the found charge carrier density distribution is output for evaluation or further processing.

A radiation dose for a therapy can subsequently be defined in a spatially resolved manner, for example on the basis of the determined charge carrier density distribution ($\rho_e$; Z).

FIG. 2 shows a flow diagram with which step 1.III, which comprises determining the minimum of the target function ZF, is illustrated in detail.

The minimum can be determined, for example, by an iterative approximation method. For example, the method of gradient descent can be used. In a step 1.IIIa a start distribution ($\rho_e$; Z)$_0$ of the charge carrier or charge carrier densities of the electrons and nuclear charges is firstly defined in the course of this approximation method.

Furthermore, in step 1.IIIa firstly approximate values $\rho_{e,M1}$, $\rho_{e,M2}$, $Z_{M1}$ and $Z_{M2}$ are defined for the charge carrier density distributions of the first material $M_1$ and the second material $M_2$ for electrons e or nuclear charges Z. For this purpose, firstly CT values or image data $I_M$ are/is determined on the basis of the acquired projection scan data $P_M$ with the aid of a filtered back projection Q:

$$I_M = QP_M. \quad (3)$$

Furthermore, the CT values $I_M$ obtained are mapped with the aid of a simple table onto the approximate values $\rho_{e,M1}$, $\rho_{e,M2}$, $Z_{M1}$, $Z_{M2}$ of distributions of charge carrier densities. The start distribution ($\rho_e$; Z)$_0$ can also be defined using the approximate values $\rho_{e,M1}$, $\rho_{e,M2}$, $Z_{M1}$, $Z_{M2}$ by simply adding the respective distributions $\rho_{e,M1}$, $\rho_{e,M2}$ or $Z_{M1}$, $Z_{M2}$.

In a sub-step 1.IIIb, starting from the start distribution ($\rho_e$; Z)$_0$, an approximated charge carrier distribution is then calculated in each iteration loop in an iterative approximation per gradient descent $$(\rho_e; Z)_{k+1} = (\rho_e; Z)_k + \alpha((\Delta\rho_e)_k; (\Delta Z)_k) \quad (4)$$

where the correction term is as follows $$((\Delta\rho_e)_k; (\Delta Z)_k) = P_S^T(P_M - P_S\{(\rho_e; Z)_k\}) \quad (5)$$

$P_S^T$ is an operator transposed to the spectral forward projector $P_S$ and $\alpha$ is an increment of the gradient descent.

The transposed operator $P_S^T$ does not have to be known exactly. A possible replacement operator to $P_S^T$ only has to have an identical zero vector space to lead to the same limit value ($\rho_e$; Z)$_\infty$.

The correction term ($\Delta\rho_e$; $\Delta Z$)$_k$ can be approximately determined as follows:

$$\begin{aligned}(\Delta\rho_e; \Delta Z)_k &= P_S^T(P_M - P_S\{(\rho_e; Z)_k\}) \quad (6)\\ &\approx P_S^T PQ(P_M - P_S\{(\rho_e; Z)_k\})\\ &= P_S^T P(I_M - I_k)\\ &\approx (h_\rho(I_M) - h_\rho(I_k); h_z(I_M) - h_z(I_k)),\end{aligned}$$

where Q is a filtered back projection and $$I_k = QP_S((\rho_e; Z)_k) \quad (7)$$

represents a comparative value to the image data on the basis of the current charge carrier distribution ($\rho_e$; Z)$_k$ which is obtained or reconstructed in that the current charge carrier distribution ($\rho_e$; Z)$_k$ is spectrally forward projected and then back projected in a filtered manner.

Furthermore, PQ=1. In the course of iteration, the functions $h_\rho(t)$, $h_Z(t)$ are used to calculate estimated values of the charge carrier densities $\rho_e$ and Z with the aid of the variables t=$I_M$, $I_K$ determined on the basis of equations 3 and 7. Here $I_M$ represents the image data determined from the projection scan data $P_M$, and $I_k$ a corresponding comparative value on the basis of a current charge carrier distribution ($\rho_e$; Z)$_k$.

These estimated values result, for example, as $$h_\rho(t) = \begin{cases} \rho_{e,M_1} \cdot \left(\frac{t}{1000} + 1\right) & t < T_2 \\ \rho_{e,M_1} \cdot \left(\frac{T_2}{1000} + 1\right) + \frac{t - T_2}{M_2 - T_2} \cdot & \\ \left(\rho_{e,M_2} - \rho_{e,M_1} \cdot \left(\frac{T_2}{1000} + 1\right)\right) & \text{otherwise} \end{cases} \quad (8)$$

where $\rho_{e,M1}$, $\rho_{e,M2}$ are approximate estimated values of the electron densities of the first material $M_1$ or of the second material $M_2$, t is a variable for a determined CT value, $T_2$ is a threshold value which identifies the limit value for a CT value above which relevant fractions of the second material $M_2$ are present in a section of an examination region, and $$h_z(t) = \begin{cases} Z_{M_1} & t < T_2 \\ Z_{M_1} + \frac{t - T_2}{M_2 - T_2} \cdot (Z_{M_2} - Z_{M_1}) & \text{otherwise} \end{cases}, \quad (9)$$

where $Z_{M1}$ and $Z_{M2}$ are fixed approximate estimated values of the nuclear charge carrier distributions of the first material $M_1$ or of the second material $M_2$.

The functions $h_\rho(t)$, $h_z(t)$ are examples of mappings of CT values on electron density distributions or nuclear charge carrier distributions. Equations 8 and 9 are based on a method for determining charge carrier density distributions, and this is described in DE 10 2015 225 395.3. Within the scope of the described method according to an example embodiment of the invention, these mappings are only used for calculating the correction term $(\Delta\rho_e)_k$; $(\Delta Z)_k)$ in the iteration, however. Only qualitative properties of the functions $h_\rho(t)$, $h_z(t)$ play a part here and the achievable accuracy of the reconstructed distributions is determined by the quality of the spectral forward projector $P_S$. This can be due to the fact that with the iteration in sub-step 1.IIIb, the convergence point fulfils the condition $P_M - P_S\{(\rho_e; Z)\} = 0$ irrespective of the mappings $h_\rho(t)$ and $h_z(t)$. These play a part only to the extent that they decide whether, in principle, the iteration converges in the solution.

In detail, estimated values $h_\rho$, $h_z$ of the electron density distribution and the nuclear charge carrier density distribution are determined firstly in a step 1.IIIba, using the approximate values $\rho_{e,M1}$, $\rho_{e,M2}$, $Z_{M1}$ and $Z_{M2}$ determined in sub-step 1.IIIa and additionally on the basis of the start distribution $(\rho_e; Z)_0$ of the electrons and nuclear charge carriers and equations 3, 7, 8 and 9 in sub-step 1.IIIb.

A correction term $(\Delta\rho_e; \Delta Z)_0$ for correcting the start distribution $(\rho_e; Z)_0$ is then determined in step 1.IIIbb according to equation 6.

A first approximated charge carrier distribution $(\rho_e; Z)_1$ is then determined in step 1.IIIbc on the basis of the correction term $(\Delta\rho_e; \Delta Z)_0$ and the start distribution $(\rho_e; Z)_0$ according to equation 4.

It is subsequently checked in step 1.IIIbd whether the convergence point of the iterative approximation process is attained according to the condition $P_M - P_S\{(\rho_e; Z)\} = 0$. This can be achieved, for example, in that a check is made as to whether a predetermined minimum value SW is fallen below when the approximated charge carrier distribution $(\rho_e; Z)_1$ is inserted in the condition for the convergence point. If this is the case, and this is identified in FIG. 2 by "j", then the process skips to step 1.IIIc in which the last-determined charge carrier distribution $(\rho_e; Z)_1$ is defined as the definitive charge carrier density distribution $(\rho_e; Z)$. If the minimum value has not yet been fallen below, and this is identified in FIG. 2 by "n", then the control variable k is increased by the value 1 in step 1.IIIbe and the process returns to step 1.IIIba and a new estimated values $h_\rho$, $h_z$ of the electron density distribution and the nuclear charge carrier density distribution is determined, albeit now on the basis of the approximated charge carrier density distribution $(\rho_e; Z)_1$.

A correction term $(\Delta\rho_e; \Delta Z)_1$ is then calculated again in step 1.IIIbb, and in step 1.IIIbc, on the basis of the correction term $(\Delta\rho_e; \Delta Z)_1$ and the current approximated charge carrier density distribution $(\rho_e; Z)_1$, a refined charge carrier density distribution $(\rho_e; Z)_2$, etc. is determined until it has been determined in step 1.IIIbd that the currently determined approximated charge carrier density distribution $(\rho_e; Z)_{k+1}$ corresponds to the threshold value criterion. The process then skips to step 1.IIIc and the last-determined approximated charge carrier density distribution $(\rho_e; Z)_{k+1}$ is defined as the definitive charge carrier density distribution $(\rho_e; Z)$.

FIG. 3 illustrates as a specific form of a material property distribution-determining device, a charge carrier density distribution-determining device 30 according to an example embodiment of the invention. The charge carrier density distribution-determining device 30 has an input data interface 31 for acquiring projection scan data $P_M$ and image data $I_M$, which was reconstructed on the basis of the projection scan data $P_M$, for example in a reconstruction unit 25 (see FIG. 5). The acquired projection scan data $P_M$ is transferred to a target function-determining unit 32. On the basis of the projection scan data $P_M$, the target function-determining unit 32 determines a target function Z which comprises a forward projection $P_S$ of a sought charge carrier density distribution $(\rho_e, Z)$ and the acquired projection scan data $P_M$. The target function ZF and the acquired image data $I_M$ are transferred to a charge carrier density distribution-determining unit 40 which, in the manner described in conjunction with FIG. 2, determines a charge carrier density distribution $(\rho_e; Z)$ for which the target function ZF assumes a minimum value. The determined data relating to the charge carrier density distribution $(\rho_e; Z)$ is then output via an output interface 33.

FIG. 4 schematically illustrates a charge carrier density distribution-determining unit 40 according to an example embodiment of the invention. The charge carrier density distribution-determining unit 40 comprises a charge carrier density distribution-estimating unit 41, which is adapted to determine approximate values $\rho_{e,M1}$, $\rho_{e,M2}$, $Z_{M1}$ and $Z_{M2}$ for the charge carrier density distributions of the first material and the second material for electrons or nuclear charges on the basis of the received image data $I_M$.

For this purpose, the CT values of the image data $I_M$ are mapped with the aid of a simple table onto the approximate values $\rho_{e,M1}$, $\rho_{e,M2}$, $Z_{M1}$, $Z_{M2}$ of distributions of charge carrier densities. A start distribution $(\rho_e; Z)_0$ is also defined using the approximate values $\rho_{e,M1}$, $\rho_{e,M2}$, $Z_{M1}$, $Z_{M2}$ by simply adding the respective distributions $\rho_{e,M1}$, $\rho_{e,M2}$ or $Z_{M1}$, $Z_{M2}$.

The approximate values $\rho_{e,M1}$, $\rho_{e,M2}$ or $Z_{M1}$, $Z_{M2}$ and the image data $I_M$ and the start distribution $(\rho_e; Z)_0$ are then transferred to an estimated value-determining unit 42 which determines on the basis of the approximate values $\rho_{e,M1}$, $\rho_{e,M2}$, $Z_{M1}$ and $Z_{M2}$, the image data $I_M$ and also on the basis of the start distribution $(\rho_e; Z)_0$, the electron densities and nuclear charge carrier densities, estimated values $h_\rho(I_M)$, $h_\rho(I_k)$ $h_z(I_M)$, $h_z(I_k)$ of the distributions of the electron densities and the nuclear charge densities. The determined estimated values $h_\rho(I_M)$, $h_\rho(I_k)$ $h_z(I_M)$, $h_z(I_k)$ are transferred to a correction term-determining unit 43 which determines a correction term $(\Delta\rho_e; \Delta Z)_k$ on the basis of the received estimated values $h_\rho(I_M)$, $h_\rho(I_k)$ $h_z(I_M)$, $h_z(I_k)$ according to equation 6. The determined correction term $(\Delta\rho_e; \Delta Z)_k$ is transferred to an approximate value-determining unit 44 which determines on the basis of the correction term $(\Delta\rho_e; \Delta Z)_k$ and on the basis of the start distribution $(\rho_e; Z)_0$, a first approximate charge carrier density distribution $(\rho_e; Z)_1$. The determined approximate charge carrier density distribution $(\rho_e; Z)_1$ is then checked by a test unit 45 as to whether it satisfies a threshold value criterion, i.e., whether a threshold value SW is fallen below when the found approximate charge carrier density distribution $(\rho_e; Z)_1$ is inserted in the convergence condition, which was described in step 1.IIIbd in conjunction with FIG. 2. If this is not yet the case, the approximate charge carrier density distribution $(\rho_e; Z)_1$ is transferred to the estimated value-determining unit 42 and there the currently determined approximate charge carrier density distribution $(\rho_e; Z)_1$ is used as the basis for determining the estimated values $h_z(I_k)$, $h_\rho(I_k)$ of the distributions of the electrons and the nuclear charges instead of the start distribution $(\rho_e; Z)_0$. If after k+1 iterations an approximate charge carrier density distribution $(\rho_e; Z)_{k+1}$ is found, which satisfies the described threshold value criterion of the test unit 45, then this distribution $(\rho_e; Z)_{k+1}$ is transferred to a density distribution-defining unit 46 and defined by the density distribution-defining unit 46 as the sought charge carrier density distribution $(\rho_e; Z)$. The found charge carrier density distribution $(\rho_e; Z)$ is then passed to the output interface 33 (see FIG. 3).

FIG. 5 schematically illustrates a computer tomography system (CT system) 1 having an inventive charge carrier density distribution-determining device 30 according to an example embodiment of the invention. The CT system is used for recording projection scan data $P_M$ from an examination region of a patient who is to subsequently be irradiated in the course of radiotherapy. Using the CT scan, a charge carrier density distribution is to be determined in the region to be examined with the aid of an example embodiment of the inventive method.

The CT system 1 essentially comprises a scanning unit 10 in which a projection data acquisition unit 5 having a detector 16 and an X-ray source 15 opposing the detector 16 rotates on a gantry 11 around a scan space 12. In front of the scanning unit 10 is located a patient-positioning device 3 or an examination table 3 whose upper part 2 can be pushed with a patient O located thereon toward the scanning unit 10 in order to move the patient O through the scan space 12 relative to the detector system 16. The scanning unit 10 and examination table 3 are controlled by a controller 20, from which acquisition control signals AS issue via a conventional control interface 24 to conventionally control the entire system according to specified scan protocols. The movement of the patient O in the z direction, which corresponds to the system axis z longitudinally through the scan space 12, and the simultaneous rotation of the X-ray source 15 produce a helix path for the X-ray source 15 relative to the patient O during the scan. At the same time the detector 16 runs along as well, always opposite the X-ray source 15, to acquire projection scan data $P_M$ which is then used for the reconstruction of volume and/or slice image data $I_M$. A sequential scanning method can be carried out as well in which a fixed position is approached in the z direction and then during a rotation, a partial rotation or a plurality of rotations, the required projection scan data $P_M$ is acquired at the relevant z position in order to reconstruct a sectional image at this z position or to reconstruct volume image data from the projection data of a plurality of z positions. At least one embodiment of the inventive method can basically also be used on other CT systems, for example with a detector that forms a complete ring.

The scan projection data $P_M$ (hereinafter also called raw data) from an examination region of the patient O acquired by the detector 16 is passed via a raw data interface 23 to the controller 20. This raw data $P_M$ is then reconstructed by a reconstruction device 25 firstly into image data $I_M$ and then transferred together with the image data $I_M$ to the charge carrier density distribution-determining device 30. A charge carrier density distribution $(\rho; Z)$ is determined there as described in conjunction with FIG. 1 to FIG. 4.

From there the data in respect of the charge carrier density distribution $(\rho; Z)$ can be graphically displayed, for example on a screen, or also be forwarded to external analysis devices or therapy planning devices (not shown), for example for planning irradiation of a tumor of the patient O.

Finally reference is again made to the fact that the described methods and the devices are merely preferred example embodiments of the invention and that the invention can be varied by a person skilled in the art without departing from the scope of the invention insofar as it is specified by the claims. Therefore, the method and material property distribution-determining device have primarily been described using a determination of charge carrier density distributions. However, the invention is not limited to an application to charge carrier density distribution but can basically also be applied to the determination of other material properties, such as, for example, the determination of attenuation coefficients or of absorption properties. For the sake of completeness reference is made to the fact that use of the indefinite article "a" or "an" does not preclude the relevant features from also being present multiple times. Similarly, the term "unit" does not preclude this from comprising a plurality of components which may optionally also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a spatial distribution of a material property value in an examination region of an examination object, the method comprising:
   acquiring projection scan data, produced using a single-energy CT scan with a defined X-ray energy spectrum from the examination region of the examination object using a defined scan projection geometry;
   establishing a target function including a spectral forward projection of a target spatial distribution and the acquired projection scan data; and
   determining the spatial distribution of a material property value by optimizing the target function such that the target function assumes an extremal value,
      wherein a projection geometry corresponding to a scan projection geometry of the acquired projection scan data is assumed for the spectral forward projection and line integrals, whose value corresponds to an absorption of X-ray radiation in a respective projection direction, are calculated from a spatial distribution of a material property value for an X-ray spectrum with the spectral forward projection by taking into account physical absorption processes that occur during the single-energy CT scan.

2. The method of claim 1, wherein the spatial distribution of the material property value is presentable as a distribution based on a distribution of at least two different base materials.

3. The method of claim 1, wherein the spatial distribution of a material property value comprises a charge carrier density distribution.

4. The method of claim 1, wherein, for optimization, the determining of the spatial distribution of a material property value, for which the target function assumes an extremal value, comprises an iterative approximation method.

5. The method of claim 1, wherein the target function comprises a standard of a difference of a spectral forward projection of a target spatial distribution of a material property value and the acquired projection scan data.

6. The method of claim 4, wherein during a first iteration step of the method, a start distribution of a material property value is used as an approximated spatial distribution of a material property value and, in addition, a correction term for further iterative approximation to the target spatial distribution of a material property value is determined.

7. The method of claim 6, wherein the correction term has a transposed spectral forward projection of a difference of the acquired projection scan data and a spectral forward projection of the approximated spatial distribution of a material property value.

8. The method of claim 6, wherein the correction term is approximately determined based upon estimated values of the spatial distribution of a material property value.

9. The method of claim 8, wherein the estimated values of the spatial distribution of a material property value are determined based upon image data, reconstructed based on the acquired projection scan data, and based on comparative values obtained by a spectral forward projection and a subsequent filtered back projection of the approximated spatial distribution of a material property value.

10. The method of claim 4, wherein an iteration of the iterative approximation method is terminated and a last-determined approximated spatial distribution of a material property value is defined as the target spatial distribution of a material property value if a standard of a difference of a spectral forward projection of the approximated spatial distribution of a material property value and the acquired projection data falls below a threshold value.

11. A material property distribution-determining device, comprising:
at least one processor configured to
acquire projection scan data, produced using a single-energy CT scan with a defined X-ray energy spectrum from an examination region of an examination object using a defined scan projection geometry;
establish a target function including a spectral forward projection of a target spatial distribution of a material property value and the acquired projection scan data; and
determine a spatial distribution of a material property by optimizing the target function in such that the target function assumes an extremal value,
wherein a projection geometry corresponding to a scan projection geometry of the acquired projection scan data is assumed for the spectral forward projection and line integrals, whose value corresponds to an absorption of X-ray radiation in a respective projection direction, are calculated from a spatial distribution of a material property value for an X-ray spectrum with the spectral forward projection by taking into account physical absorption processes that occur during the single-energy CT scan.

12. A computer tomography system, comprising:
a scanner to scan an examination region of an object to be examined;
a controller to control the scanner; and
the material property distribution-determining device of claim 11.

13. A non-transitory computer-readable medium including a computer program, directly loadable into a storage unit of a computer tomography system, including program segments to carry out the method of claim 1 when the computer program is run in the computer tomography system.

14. A non-transitory computer-readable medium storing program segments, readable and runable by a process unit, to carry out the method of claim 1 when the program segments are run by the process unit.

15. The method of claim 3, wherein the charge carrier density distribution is a density distribution of at least one of electrons and nuclear charges.

16. The method of claim 15, wherein the charge carrier density distribution is a density distribution of at least one of electrons and nuclear charges of at least two different materials.

17. The method of claim 2, wherein the spatial distribution of a material property value comprises a charge carrier density distribution.

18. The method of claim 17, wherein the charge carrier density distribution is a density distribution of at least one of electrons and nuclear charges.

19. The method of claim 18, wherein the charge carrier density distribution is a density distribution of at least one of electrons and nuclear charges of at least two different materials.

20. The method of claim 4, wherein the iterative approximation method is a gradient descent method.

21. The method of claim 5, wherein during a first iteration step of the method, a start distribution of a material property value is used as an approximated spatial distribution of a material property value and, in addition, a correction term for further iterative approximation to the target spatial distribution of a material property value is determined.

22. The method of claim 21, wherein the correction term has a transposed spectral forward projection of a difference of the acquired projection scan data and a spectral forward projection of the approximated spatial distribution of a material property value.

23. The method of claim 7, wherein the correction term is approximately determined based upon estimated values of the spatial distribution of a material property value.

24. The method of claim 23, wherein the estimated values of the spatial distribution of a material property value are determined based upon image data, reconstructed based on the acquired projection scan data, and based on comparative values obtained by a spectral forward projection and a subsequent filtered back projection of the approximated spatial distribution of a material property value.

25. A non-transitory computer-readable medium including a computer program, directly loadable into a storage unit of a computer tomography system, including program segments to carry out the method of claim 4 when the computer program is run in the computer tomography system.

26. A non-transitory computer-readable medium storing program segments, readable and runable by a process unit, to carry out the method of claim 4 when the program segments are run by the process unit.

* * * * *